(12) United States Patent
May et al.

(10) Patent No.: US 8,569,007 B2
(45) Date of Patent: Oct. 29, 2013

(54) METHOD FOR REDUCING THE APPEARANCE OF FALSE POSITIVE BANDS IN SDS-PAGE ANALYSIS OF PROTEOLYTIC DIGESTION OF A SAMPLE

(75) Inventors: Kimberly Margaret Louise May, Scotch Plains, NJ (US); Susan V. Cannon-Carlson, Wayne, NJ (US); Brittany Charlotte Larkin, Clark, NJ (US); Collette Marie Cutler, Bloomingdale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/343,274

(22) Filed: Jan. 4, 2012

(65) Prior Publication Data

US 2012/0103810 A1    May 3, 2012

Related U.S. Application Data

(63) Continuation of application No. 12/001,658, filed on Dec. 11, 2007, now abandoned.

(60) Provisional application No. 60/874,191, filed on Dec. 11, 2006.

(51) Int. Cl.
*C12Q 1/37*    (2006.01)

(52) U.S. Cl.
USPC .......................................................... 435/23

(58) Field of Classification Search
USPC .......................................................... 435/23
See application file for complete search history.

(56) References Cited

U.S. PATENT DOCUMENTS

2004/0018191 A1    1/2004    Wang et al.
2006/0177887 A1    8/2006    Miyazaki et al.

FOREIGN PATENT DOCUMENTS

| WO | WO01/11016 | 2/2001 |
|---|---|---|
| WO | WO01/23527 | 4/2001 |
| WO | WO2006/123926 | 11/2006 |
| WO | WO2008/063472 | 5/2008 |

OTHER PUBLICATIONS

Burteau, Caroline C., et al.; "Fortification of a protein-free cell culture medium with plant peptones improves cultivation and productivity of an interferon-gamma-producing cho cell line"; In Vitro Cellular & Developmental Biology; 39(7):291-296 (2003).
Chun, Bok-Hwan, et al.; "Usability of size-excluded fractions of soy protein hydrolysates for growth and viability of Chinese hamster ovary cells in protein-free suspension culture"; Bioresource Technology; 98(5):1000-1005 (2007).
Franek, Frantisek, et al.; "Plant protein hydrosylates: preparation of defined peptide fractions promoting growth and production in animal cells cultures"; Biotechnology Progress; 16(5):688-692 (2000).
Grenier, Daniel, et al., "Characterization of sodium dodecyl sulfate-stable Bacteroides gingivalis proteases by polyacrylamide gel electrophoresis"; Infect Immun. Jan. 1989;57(1):95-9.
Heidemann, Rudiger, et al.; "The use of peptones as medium additives for the production of a recombinant therapeutic protein in high density perfusion cultures of mammalian cells"; Cytotechnology; 32(2):157-167 (2000).
International Search Report for corresponding International Application No. PCT/US2007/025320 dated Jun. 11, 2008.
Kim, Do Yun, et al.; "Development of serum-free media for a recombinant CHO cell line producing recombinant antibody"; Enzyme and Microbial Technology; 39(3):426-433 (2006).
Mols, J., et al.; "Origin of rice protein hydrolysates added to protein-free media alters secretion and extracellular proteolysis of recombinant interferon-γ as well as CHO-320 cell growth"; Biotechnology Letters; 26:1043-1046 (2004).
Schlaeger, Ernst-Jurgen; "The protein hydrolysate, Primatone RL, is a cost-effective multiple growth promoter of mammalian cell culture in serum-containing and serum-free media and displays anti-apoptosis properties"; Journal of Immunological Methods; 194(2):191-199 (1996).

*Primary Examiner* — Ralph Gitomer

(57)    ABSTRACT

The present invention includes a method for reducing the appearance of false positive bands in SDS-PAGE analysis of proteolytic digestion, of a sample that comprises an immunoglobulin polypeptide, at pH 8.8.

12 Claims, 5 Drawing Sheets

SEQUENCE LISTING

```
<160> NUMBER OF SEQ ID NOS: 12

<210> SEQ ID NO 1
<211> LENGTH: 384
<212> TYPE: DNA
<213> ORGANISM: Homo sapiens
<220> FEATURE:
<221> NAME/KEY: CDS
<222> LOCATION: (1)..(384)
<220> FEATURE:
<221> NAME/KEY: mat_peptide
<222> LOCATION: (58)..(384)

<400> SEQUENCE: 1 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
            -15                 -10                  -5 tcc agg ggt gaa att gtg ctg act cag agc cca gac tct ctg tct gtg      96
Ser Arg Gly Glu Ile Val Leu Thr Gln Ser Pro Asp Ser Leu Ser Val
         -1  1               5                  10 act cca ggc gag aga gtc acc atc acc tgc cgg gcc agt cag agc att     144
Thr Pro Gly Glu Arg Val Thr Ile Thr Cys Arg Ala Ser Gln Ser Ile
     15                  20                  25 ggt agt agc tta cac tgg tac cag cag aaa cca ggt cag tct cca aag     192
Gly Ser Ser Leu His Trp Tyr Gln Gln Lys Pro Gly Gln Ser Pro Lys
 30                  35                  40                  45 ctt ctc atc aag tat gca tcc cag tcc ctc tca ggg gtc ccc tcg agg     240
Leu Leu Ile Lys Tyr Ala Ser Gln Ser Leu Ser Gly Val Pro Ser Arg
                 50                  55                  60 ttc agt ggc agt gga tct ggg aca gat ttc acc ctc acc atc agt agc     288
Phe Ser Gly Ser Gly Ser Gly Thr Asp Phe Thr Leu Thr Ile Ser Ser
                 65                  70                  75 ctc gag gct gaa gat gct gca gcg tat tac tgt cat cag agt agt cgt     336
Leu Glu Ala Glu Asp Ala Ala Ala Tyr Tyr Cys His Gln Ser Ser Arg
             80                  85                  90 tta cct cac act ttc ggc caa ggg acc aag gtg gag atc aaa cgt acg     384
Leu Pro His Thr Phe Gly Gln Gly Thr Lys Val Glu Ile Lys Arg Thr
     95                 100                 105

<210> SEQ ID NO 2
<211> LENGTH: 128
<212> TYPE: PRT
<213> ORGANISM: Homo sapiens

<400> SEQUENCE: 2

Met Ser Pro Ser Gln Leu Ile Gly Phe Leu Leu Leu Trp Val Pro Ala
            -15                 -10                  -5

Ser Arg Gly Glu Ile Val Leu Thr Gln Ser Pro Asp Ser Leu Ser Val
         -1  1               5                  10

Thr Pro Gly Glu Arg Val Thr Ile Thr Cys Arg Ala Ser Gln Ser Ile
     15                  20                  25

Gly Ser Ser Leu His Trp Tyr Gln Gln Lys Pro Gly Gln Ser Pro Lys
 30                  35                  40                  45

Leu Leu Ile Lys Tyr Ala Ser Gln Ser Leu Ser Gly Val Pro Ser Arg
                 50                  55                  60
```

```
Phe Ser Gly Ser Gly Ser Gly Thr Asp Phe Thr Leu Thr Ile Ser Ser
            65                  70                  75

Leu Glu Ala Glu Asp Ala Ala Ala Tyr Tyr Cys His Gln Ser Ser Arg
            80                  85                  90

Leu Pro His Thr Phe Gly Gln Gly Thr Lys Val Glu Ile Lys Arg Thr
            95                 100                 105

<210> SEQ ID NO 3
<211> LENGTH: 384
<212> TYPE: DNA
<213> ORGANISM: Homo sapiens
<220> FEATURE:
<221> NAME/KEY: CDS
<222> LOCATION: (1)..(384)
<220> FEATURE:
<221> NAME/KEY: mat_peptide
<222> LOCATION: (1)..(384)

<400> SEQUENCE: 3 atg tcg cca tca caa ctc att ggg ttt ctg ctg ctc tgg gtt cca gcc     48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg     96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att    144
Thr Pro Gly Glu Arg Val Thr Ile Thr Cys Arg Ala Ser Gln Ser Ile
        35                  40                  45 ggt agt agc tta cac tgg tac cag cag aaa cca ggt cag tct cca aag    192
Gly Ser Ser Leu His Trp Tyr Gln Gln Lys Pro Gly Gln Ser Pro Lys
    50                  55                  60 ctt ctc atc aag tat gca tcc cag tcc ctc tca ggg gtc ccc tcg agg    240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc    288
Phe Ser Gly Ser Gly Ser Gly Thr Asp Phe Thr Leu Thr Ile Ser Ser
                85                  90                  95 ctc gag gct gaa gat ttc gca gtg tat tac tgt cat cag agt agt cgt    336
Leu Glu Ala Glu Asp Phe Ala Val Tyr Tyr Cys His Gln Ser Ser Arg
            100                 105                 110 tta cct cac act ttc ggc caa ggg acc aag gtg gag atc aaa cgt acg    384
Leu Pro His Thr Phe Gly Gln Gly Thr Lys Val Glu Ile Lys Arg Thr
        115                 120                 125

<210> SEQ ID NO 4
<211> LENGTH: 128
<212> TYPE: PRT
<213> ORGANISM: Homo sapiens

<400> SEQUENCE: 4

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
```

```
                    85                  90                  95
Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 5
<211> LENGTH: 384
<212> TYPE: DNA
<213> ORGANISM: Homo sapiens
<220> FEATURE:
<221> NAME/KEY: CDS
<222> LOCATION: (1)..(384)
<220> FEATURE:
<221> NAME/KEY: mat_peptide
<222> LOCATION: (58)..(384)

<400> SEQUENCE: 5 atg tcg cca tca caa ctc att ggg ttt ctg ctg ctc tgg gtt cca gcc     48
Met Ser Pro Ser Gln Leu Ile Gly Phe Leu Leu Leu Trp Val Pro Ala
            -15                 -10                 -5 tcc agg ggt gaa att gtg ctg act cag agc cca ggt acc ctg tct gtg     96
Ser Arg Gly Glu Ile Val Leu Thr Gln Ser Pro Gly Thr Leu Ser Val
    -1  1                   5                   10 tct cca ggc gag aga gcc acc ctc tcc tgc cgg gcc agt cag agc att    144
Ser Pro Gly Glu Arg Ala Thr Leu Ser Cys Arg Ala Ser Gln Ser Ile
 15                  20                  25 ggt agc agc tta cac tgg tac cag cag aaa cca ggt cag gct cca agg    192
Gly Ser Ser Leu His Trp Tyr Gln Gln Lys Pro Gly Gln Ala Pro Arg
 30                  35                  40                  45 ctt ctc atc aag tat gca tcc cag tcc ctc tca ggg atc ccc gat agg    240
Leu Leu Ile Lys Tyr Ala Ser Gln Ser Leu Ser Gly Ile Pro Asp Arg
                 50                  55                  60 ttc agt ggc agt gga tct ggg aca gat ttc acc ctc acc atc agt aga    288
Phe Ser Gly Ser Gly Ser Gly Thr Asp Phe Thr Leu Thr Ile Ser Arg
             65                  70                  75 ctg gag cct gaa gat gct gca gcg tat tac tgt cat cag agt agt cgt    336
Leu Glu Pro Glu Asp Ala Ala Ala Tyr Tyr Cys His Gln Ser Ser Arg
         80                  85                  90 tta cct cac act ttc ggc caa ggg acc aag gtg gag atc aaa cgt aca    384
Leu Pro His Thr Phe Gly Gln Gly Thr Lys Val Glu Ile Lys Arg Thr
     95                 100                 105

<210> SEQ ID NO 6
<211> LENGTH: 128
<212> TYPE: PRT
<213> ORGANISM: Homo sapiens

<400> SEQUENCE: 6

Met Ser Pro Ser Gln Leu Ile Gly Phe Leu Leu Leu Trp Val Pro Ala
            -15                 -10                 -5

Ser Arg Gly Glu Ile Val Leu Thr Gln Ser Pro Gly Thr Leu Ser Val
    -1  1                   5                   10

Ser Pro Gly Glu Arg Ala Thr Leu Ser Cys Arg Ala Ser Gln Ser Ile
 15                  20                  25

Gly Ser Ser Leu His Trp Tyr Gln Gln Lys Pro Gly Gln Ala Pro Arg
 30                  35                  40                  45

Leu Leu Ile Lys Tyr Ala Ser Gln Ser Leu Ser Gly Ile Pro Asp Arg
                 50                  55                  60

Phe Ser Gly Ser Gly Ser Gly Thr Asp Phe Thr Leu Thr Ile Ser Arg
             65                  70                  75
```

```
Leu Glu Pro Glu Asp Ala Ala Ala Tyr Tyr Cys His Gln Ser Ser Arg
            80                  85                  90

Leu Pro His Thr Phe Gly Gln Gly Thr Lys Val Glu Ile Lys Arg Thr
        95                 100                 105

<210> SEQ ID NO 7
<211> LENGTH: 384
<212> TYPE: DNA
<213> ORGANISM: Homo sapiens
<220> FEATURE:
<221> NAME/KEY: CDS
<222> LOCATION: (1)..(384)
<220> FEATURE:
<221> NAME/KEY: mat_peptide
<222> LOCATION: (1)..(384)

<400> SEQUENCE: 7 atg tcg cca tca caa ctc att ggg ttt ctg ctg ctc tgg gtt cca gcc     48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg    96
Ser Arg Gly Glu Ile Val Leu Thr Gln Ser Pro Gly Thr Leu Ser Val
                20                  25                  30 tct cca ggc gag aga gcc acc ctc tcc tgc cgg gcc agt cag agc att   144
Ser Pro Gly Glu Arg Ala Thr Leu Ser Cys Arg Ala Ser Gln Ser Ile
            35                  40                  45 ggt agt agc tta cac tgg tac cag cag aaa cca ggt cag gct cca agg   192
Gly Ser Ser Leu His Trp Tyr Gln Gln Lys Pro Gly Gln Ala Pro Arg
        50                  55                  60 ctt ctc atc aag tat gca tcc cag tcc ctc tca ggg atc ccc gat agg   240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga   288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt   336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca   384
Leu Pro His Thr Phe Gly Gln Gly Thr Lys Val Glu Ile Lys Arg Thr
        115                 120                 125

<210> SEQ ID NO 8
<211> LENGTH: 128
<212> TYPE: PRT
<213> ORGANISM: Homo sapiens

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
                20                  25                  30

Ser Pro Gly Glu Arg Ala Thr Leu Ser Cys Arg Ala Ser Gln Ser Ile
            35                  40                  45

Gly Ser Ser Leu His Trp Tyr Gln Gln Lys Pro Gly Gln Ala Pro Arg
        50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110
```

```
Leu Pro His Thr Phe Gly Gln Gly Thr Lys Val Glu Ile Lys Arg Thr
        115                 120                 125

<210> SEQ ID NO 9
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 9 atg gag ttt ggg ctg agc tgg gtt ttc ctt gtt gct ata tta aaa ggt      48
Met Glu Phe Gly Leu Ser Trp Val Phe Leu Val Ala Ile Leu Lys Gly
        -15                 -10                 -5 gtc cag tgt gag gtt cag ctg gtg cag tct ggg gga ggc ttg gta aag      96
Val Gln Cys Glu Val Gln Leu Val Gln Ser Gly Gly Gly Leu Val Lys
        -1  1                5                  10 cct ggg ggg tcc ctg aga ctc tcc tgt gca gcc tct gga ttc acc ttc     144
Pro Gly Gly Ser Leu Arg Leu Ser Cys Ala Ala Ser Gly Phe Thr Phe
 15                  20                  25 agt agc ttt gct atg cac tgg gtt cgc cag gct cca gga aaa ggt ctg     192
Ser Ser Phe Ala Met His Trp Val Arg Gln Ala Pro Gly Lys Gly Leu
 30                  35                  40                  45 gag tgg ata tca gtt att gat act cgt ggt gcc aca tac tat gca gac     240
Glu Trp Ile Ser Val Ile Asp Thr Arg Gly Ala Thr Tyr Tyr Ala Asp
                 50                  55                  60 tcc gtg aag ggc cga ttc acc atc tcc aga gac aat gcc aag aac tcc     288
Ser Val Lys Gly Arg Phe Thr Ile Ser Arg Asp Asn Ala Lys Asn Ser
         65                  70                  75 ttg tat ctt caa atg aac agc ctg aga gcc gag gac act gct gtg tat     336
Leu Tyr Leu Gln Met Asn Ser Leu Arg Ala Glu Asp Thr Ala Val Tyr
     80                  85                  90 tac tgt gca aga ctg ggg aac ttc tac tac ggt atg gac gtc tgg ggc     384
Tyr Cys Ala Arg Leu Gly Asn Phe Tyr Tyr Gly Met Asp Val Trp Gly
 95                 100                 105 caa ggg acc acg gtc acc gtc tcc tca                                 411
Gln Gly Thr Thr Val Thr Val Ser Ser
110                 115

<210> SEQ ID NO 10
<211> LENGTH: 137
<212> TYPE: PRT
<213> ORGANISM: Homo sapiens

<400> SEQUENCE: 10

Met Glu Phe Gly Leu Ser Trp Val Phe Leu Val Ala Ile Leu Lys Gly
        -15                 -10                 -5

Val Gln Cys Glu Val Gln Leu Val Gln Ser Gly Gly Gly Leu Val Lys
        -1  1                5                  10

Pro Gly Gly Ser Leu Arg Leu Ser Cys Ala Ala Ser Gly Phe Thr Phe
 15                  20                  25

Ser Ser Phe Ala Met His Trp Val Arg Gln Ala Pro Gly Lys Gly Leu
 30                  35                  40                  45

Glu Trp Ile Ser Val Ile Asp Thr Arg Gly Ala Thr Tyr Tyr Ala Asp
                 50                  55                  60

Ser Val Lys Gly Arg Phe Thr Ile Ser Arg Asp Asn Ala Lys Asn Ser
         65                  70                  75
```

```
Leu Tyr Leu Gln Met Asn Ser Leu Arg Ala Glu Asp Thr Ala Val Tyr
        80                  85                  90

Tyr Cys Ala Arg Leu Gly Asn Phe Tyr Tyr Gly Met Asp Val Trp Gly
 95                 100                 105

Gln Gly Thr Thr Val Thr Val Ser Ser
110                 115

<210> SEQ ID NO 11
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 11 atg gag ttt ggg ctg agc tgg gtt ttc ctt gtt gct ata tta aaa ggt    48
Met Glu Phe Gly Leu Ser Trp Val Phe Leu Val Ala Ile Leu Lys Gly
            -15                 -10                  -5 gtc cag tgt gag gtt cag ctg gtg cag tct ggg gga ggc ttg gta cag    96
Val Gln Cys Glu Val Gln Leu Val Gln Ser Gly Gly Gly Leu Val Gln
         -1  1               5                  10 ccc ggg ggg tcc ctg aga ctc tcc tgt gca gcc tct gga ttc acc ttc   144
Pro Gly Gly Ser Leu Arg Leu Ser Cys Ala Ala Ser Gly Phe Thr Phe
         15                  20                  25 agt agc ttt gct atg cac tgg gtt cgc cag gct cca gga aaa ggt ctg   192
Ser Ser Phe Ala Met His Trp Val Arg Gln Ala Pro Gly Lys Gly Leu
 30                  35                  40                  45 gag tgg ata tca gtt att gat act cgt ggt gcc aca tac tat gca gac   240
Glu Trp Ile Ser Val Ile Asp Thr Arg Gly Ala Thr Tyr Tyr Ala Asp
                 50                  55                  60 tcc gtg aag ggc cga ttc acc atc tcc aga gac aat gcc aag aac tcc   288
Ser Val Lys Gly Arg Phe Thr Ile Ser Arg Asp Asn Ala Lys Asn Ser
             65                  70                  75 ttg tat ctt caa atg aac agc ctg aga gcc gag gac act gct gtg tat   336
Leu Tyr Leu Gln Met Asn Ser Leu Arg Ala Glu Asp Thr Ala Val Tyr
         80                  85                  90 tac tgt gca aga ctg ggg aac ttc tac tac ggt atg gac gtc tgg ggc   384
Tyr Cys Ala Arg Leu Gly Asn Phe Tyr Tyr Gly Met Asp Val Trp Gly
 95                 100                 105 caa ggg acc acg gtc acc gtc tcc tca                               411
Gln Gly Thr Thr Val Thr Val Ser Ser
110                 115

<210> SEQ ID NO 12
<211> LENGTH: 137
<212> TYPE: PRT
<213> ORGANISM: Homo sapiens

<400> SEQUENCE: 12

Met Glu Phe Gly Leu Ser Trp Val Phe Leu Val Ala Ile Leu Lys Gly
            -15                 -10                  -5

Val Gln Cys Glu Val Gln Leu Val Gln Ser Gly Gly Gly Leu Val Gln
         -1  1               5                  10

Pro Gly Gly Ser Leu Arg Leu Ser Cys Ala Ala Ser Gly Phe Thr Phe
         15                  20                  25

Ser Ser Phe Ala Met His Trp Val Arg Gln Ala Pro Gly Lys Gly Leu
 30                  35                  40                  45

Glu Trp Ile Ser Val Ile Asp Thr Arg Gly Ala Thr Tyr Tyr Ala Asp
```

-continued

```
                50                      55                      60
Ser Val Lys Gly Arg Phe Thr Ile Ser Arg Asp Asn Ala Lys Asn Ser
            65                      70                      75

Leu Tyr Leu Gln Met Asn Ser Leu Arg Ala Glu Asp Thr Ala Val Tyr
        80                      85                      90

Tyr Cys Ala Arg Leu Gly Asn Phe Tyr Tyr Gly Met Asp Val Trp Gly
    95                      100                     105

Gln Gly Thr Thr Val Thr Val Ser Ser
110                     115
```

METHOD FOR REDUCING THE APPEARANCE OF FALSE POSITIVE BANDS IN SDS-PAGE ANALYSIS OF PROTEOLYTIC DIGESTION OF A SAMPLE

This application is a continuation of U.S. patent application Ser. No. 12/001,658; filed Dec. 11, 2007 now abandoned, which claims the benefit of U.S. provisional patent application No. 60/874,191; filed Dec. 11, 2006, each of which is herein incorporated by reference in its entirety.

FIELD OF THE INVENTION

The present invention relates, inter alia, to assays and compositions for detecting proteolytic activity in a sample.

BACKGROUND OF THE INVENTION

When recombinantly expressing peptides such as antibodies, vaccines or other therapeutic polypeptides (e.g., interferon or erythropoietin), plant-derived hydrolysates are often added to the cell culture media in order to increase the titer. The small peptide chains in the hydrolysates are derived from protease-driven degradation of soy and wheat by-products of the food industry which results in the unintended introduction of proteases to the culture. The presence of the proteases leads to in culture degradation of the antibodies, particularly if engineered to be secreted into the culture. Later purification is also complicated if the proteases are not sufficiently inactivated or removed and are, instead, carried over, in an active form, to the purified product. Moreover, due to the irregular nature of the plant sources from which the hydrolysates are derived, lot-to-lot variability may also be observed. The variability makes removal or inactivation of the proteases more difficult.

During manufacture of the hydrolysates, an enzyme, often a papain-derivative, is added to a batch of soy, wheat, or rice. The enzyme is allowed to digest the food material for a specific amount of time and is then, typically, heat inactivated via a pasteurization step. For high-throughput production, heat inactivation of the enzyme is achieved using heat exchangers. The contact time, however, is minimal. For this reason, complete inactivation is not always successful. Typically, the hydrolysates are then ultrafiltered with membranes ranging in size cut-off from 10 kDa to 50 kDa. Some enzymes are not removed during this step due to inefficiency associated with ultrafiltration when used for removal of polypeptides from a sample. Leaching of the digestion enzyme into the product has been documented in the literature (Mols et al., Biotechnology Letters 26: 1043-1046 (2004)) wherein a thiol-protease was discovered in rice hydrolysates from CWBI (Centre Wallon de Biologie Industrielle) that had been ultrafiltered.

The presence of even very low levels of proteases in a peptide product can cause significant problems with respect to the quality and stability of the product over time. Slow proteolytic degradation of the product is a problem that must be monitored in order to both track product quality and stability and to develop purification procedures for complete removal of protease contamination from the product. There are known methods for detecting proteases in a sample, however, the sensitivity of such assays is relatively low. For example, culture media vendors commonly use a fluorescence-based assay with a casein peptide substrate that emits fluorescence light when cleaved by a protease. Since the quantity of protease present in a sample of purified antibody product is, generally, very low, the known protease assays are insufficient. There exists a need in the art for protease assays comprising sensitivity high enough to detect very low levels of protease activity in a sample.

SUMMARY OF THE INVENTION

The present invention addresses this need in the art, and others, for example, by providing the methods and compositions set forth herein.

The present invention provides a method for determining the presence of proteolytic activity (e.g., a protease) in a sample comprising incubating the sample with a substrate for said protease 8 or more hours and determining proteolysis of said substrate. In an embodiment of the invention, the method comprising the steps of: (a) combining the sample with a peptide substrate and, optionally, with a reducing agent; (b) incubating the sample for at least 8 hours at room temperature (e.g., about 22° C. or 28° C. (e.g., 22° C., 23° C., 24° C., 25° C., 26° C., 27° C., 28° C.)); and (c) determining proteolysis of the substrate (e.g., by heating the sample, substrate and buffer to at least 90° C. for at least 5 minutes, electrophoresing the sample, substrate and buffer on a SDS-polyacrylamide gel and staining the gel with a protein indicator stain. In an embodiment of the invention, the gel is a 4-12% or 4-20% discontinuous SDS-polyacrylamide gel. In an embodiment of the invention, about 1 µg to 12 µg (e.g., 1 µg, 2 µg, 3 µg, 4 µg, 5 µg, 6 µg, 7 µg, 8 µg, 9 µg, 10 µg, 11 µg, 12 µg) of substrate is electrophoresed on the gel. In an embodiment of the invention, the pH of said sample and the substrate is 8.8. In an embodiment of the invention, the sample and the substrate are combined with a Tris pH 8.8 buffer. In an embodiment of the invention, the sample and substrate are incubated for 18 hours. In an embodiment of the invention, the substrate is an immunoglobulin polypeptide. In an embodiment of the invention, the concentration of the immunoglobulin in (a) is about 0.3 mg/ml to 1 mg/ml. In an embodiment of the invention, proteolysis is determined by SDS-polyacrylamide gel electrophoresis analysis. In an embodiment of the invention, the substrate is anti-IGF1R antibody or anti-IL10 antibody. In an embodiment of the invention, the sample is cellular growth media. In an embodiment of the invention, the growth media comprises a hydrolysate (e.g., a plant-derived hydrolysate). The present invention also provides a method for producing an antibody comprising determining the presence of proteolytic activity in culture medium by the method set forth above and culturing host cells expressing the antibody in said medium and, optionally, isolating the antibody from the medium.

DETAILED DESCRIPTION OF THE INVENTION

Figure 1:
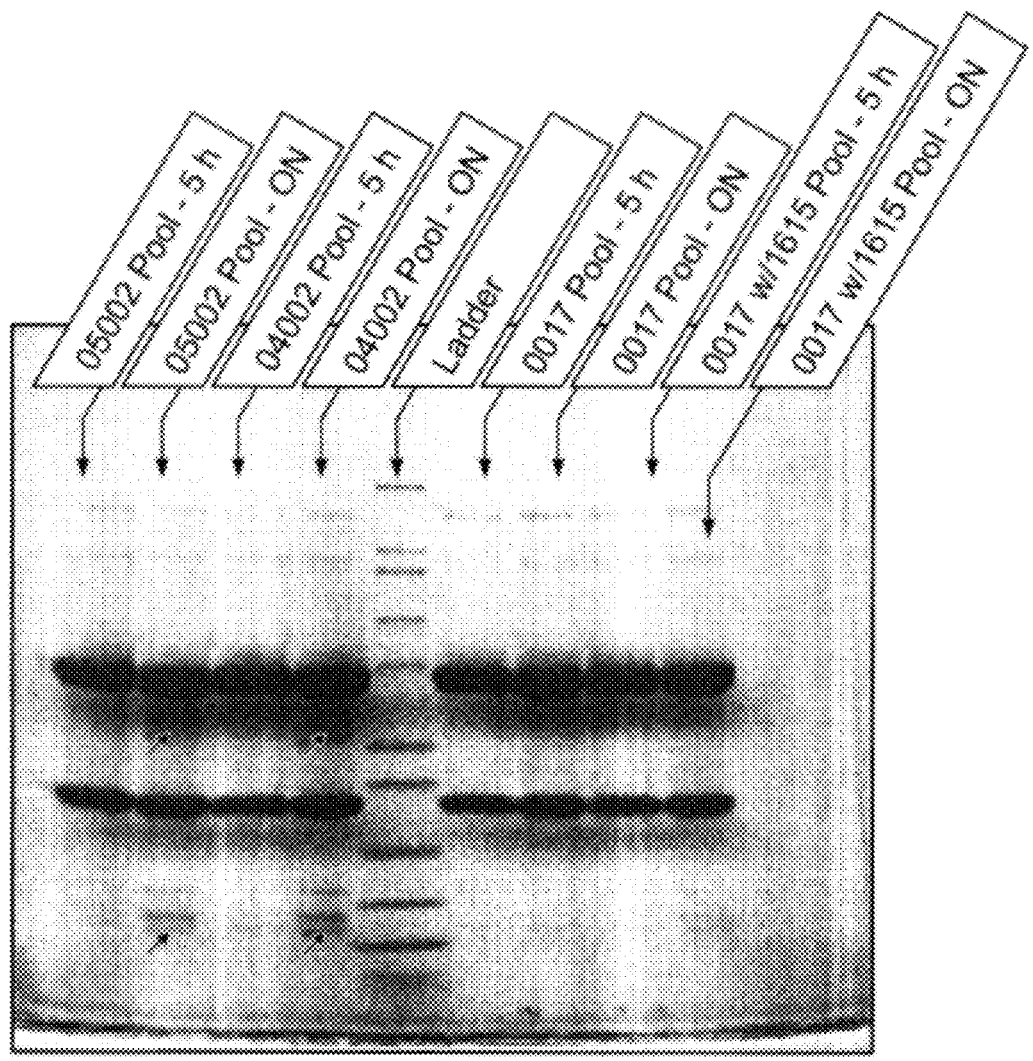
FIG. 1: Example of increased sensitivity with exposure time to sample buffer prior to boiling. Arrows indicate lanes of increased proteolysis with exposure time.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

The term "room temperature" is known in the art and, in an embodiment of the invention, is about 23° C., 24° C. or 25° C.

The methods described herein may be used to detect proteolytic activity. Proteolytic activity includes both proteolytic enzymes (proteases) as well as less specific factors which degrade or decrease the stability of polypeptides (e.g., heat, pH, physical forces).

Assays

The present invention provides a new and highly sensitive assay for determining the presence of proteases in a sample such as cellular growth media. In an embodiment of the invention, the assay is used to detect any protease including, but not limited to, thiolproteases, metalloproteases and serine proteases.

The meaning of the terms thiolprotease, metalloprotease and serine protease are well known in the art. In an embodiment of the invention, a thiolprotease (thioprotease, thiol peptidase; thiolproteinase or sulfhydryl protease) is a proteolytic enzyme with a cysteine residue (Cys) in its active site. Examples of thiolproteases include, for example, any member of the papain family (e.g., cathepsin J and cathepsin C), caspases and calpains.

In an embodiment of the invention, metalloproteases bind a divalent metal ion such as $Zn^{2+}$ or $Co^{2+}$ in their active site. Examples of metalloproteases include, for example, ADAM 33, 30, 28, 25, 24, 21, 20, 19, 17, 15, 12, 10, 26a, aminopeptidase N, aminopeptidease G, and angiotensin-converting enzyme.

In an embodiment of the invention, a serine protease is characterized by the presence of a serine residue in the active site of the enzyme. Examples of serine proteases include, for example, chymotrypsin, trypsin, elastase and subtilisin.

The present invention provides a method for determining the presence of proteolytic activity in a sample following an overnight incubation of a sample for which the presence of the protease is being determined and a substrate of the protease (e.g., in an embodiment of the invention, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours or at least about 24 hours).

The present invention encompasses any method whereby protease activity in a sample is determined comprising the step of incubating the sample with a protease substrate overnight, followed by determination of degradation of the substrate. In an embodiment of the invention, the method comprises the steps of: (a) combining the sample with a polypeptide substrate and, optionally, with a reducing agent (e.g., dithiothreitol (DTT) or β-mercaptoethanol (BME)); (b) adjusting pH of the sample and substrate to about 8.8 (e.g., by adding a buffer such as Tris pH 8.8); (c) incubating the sample overnight, for example, for at least 12 hours; and (d) determining proteolysis of the substrate, for example, by electrophoretic analysis on an SDS-PAGE gel (e.g., including the steps of electrophoreses, staining the gel with a dye, such as coomassie brilliant blue and, optionally destaining the gel and, optionally, drying the gel and, optionally, recording the gel data by, for example, photograph or computer scan).

In embodiments wherein the activity of a thiolprotease is to be determined, a reducing agent may or may not be combined with the sample and the substrate.

An embodiment of the invention also includes a method for determining non-protease mediated proteolysis. Such a method is similar to that set forth above, except that the method includes incubating the substrate (e.g., an antibody) under conditions whereby proteolysis is suspected to occur overnight. For example, the assay can be used to determine proteolytic degradation occurs under a given set of protease free buffer conditions, under high heat or extreme pH. Following incubation, proteolysis may be detected, e.g., by SDS-PAGE analysis.

A substrate for the protease to be determined can, in an embodiment of the invention, be any polypeptide. For example, if the proteolytic activity against a particular protein, such as an antibody, is of interest, the antibody can be used as the substrate.

SDS-PAGE

SDS-PAGE stands for sodium dodecyl sulfate (SDS) polyacrylamide gel electrophoresis (PAGE) and is useful for molecular weight analysis of proteins. SDS is a detergent that dissociates and unfolds oligomeric proteins into its subunits. The SDS binds to the polypeptides to form complexes with fairly constant charge to mass ratios. The electrophoretic migration rate through a gel is therefore determined only by the size of the complexes. Molecular weights are determined by simultaneously running marker proteins of known molecular weight.

SDS-PAGE analysis was initially described by Laemmli (Nature 227: 680-685 (1970)) which is herein incorporated by reference in its entirety.

Embodiments of the invention include methods wherein proteolysis is determined by continuous or discontinuous SDS-PAGE. Continuous systems use the same buffer in both the gel and tank, while discontinuous buffer systems employ different buffers for tank and gel, and often two different buffers within the gel, with a third buffer in the tank. In a discontinuous system, two sequential gels are typically used; the top gel, called the stacking gel, is, in some cases, slightly acidic (pH 6.8) and has a low (e.g., about 5%) acrylamide concentration to make a porous gel. Under these conditions proteins typically separate poorly but form thin, sharply defined bands. The lower gel, called the separating, or resolving gel, is more basic (pH 8.8), and has a higher acrylamide content (e.g., 12%), which causes the gel to have narrower channels or pores. As a protein, concentrated into sharp bands by the stacking gel, travels through the separating gel, the narrower pores have a sieving effect, allowing smaller proteins to travel more easily, and hence rapidly, than larger proteins.

For example, in an embodiment of the invention, the stacking gel comprises about 4% acrylamide whereas the resolving gel comprises about 6% to about 15% acrylamide (e.g., 6, 7, 8, 9, 10, 11, 12, 13, 14, 15). A discontinuous gel may be described as follows: stacking gel percentage of acrylamide-resolving gel percentage of acrylamide. For example, a 4-12% discontinuous gel comprises a 4% stacking gel and a 12% resolving gel.

Following electrophoresis, the proteins within the gel may be observed, visually, by staining with protein indicator stain. Common protein indicator stains are Coomassie Brilliant Blue (0.5% (mass/volume) in 50% methanol/water) and silver stain (e.g., silver nitrate based stain). Other stains include copper chloride (Lee et al., Anal. Biochem. 166: 308-312 (1987)).

In order to enhance the visual quality of the gel data, a stained gel, may be destained to remove dye present in the gel non-specifically. For example, a gel stained with coomassie blue can be destained in a methanol solution or a methanol/acetic acid solution. Glycerol may optionally be added to the destaining solution. Destaining can be performed by simply soaking the stained gel in destaining solution at room temperature or heating the gel and destaining solution, for example, in a microwave oven.

A polyacrylamide gel may also be dried and fixed to a permanent substrate such as paper for long term storage. Drying and fixing are typically performed under vacuum and in the presence of heat.

A gel may be loaded with an indicator dye which allows visual evaluation of the progress of the electrophoresis. For example, a dye such as bromophenol blue may be loaded onto a gel along with the sample. In an embodiment of the invention, the dye is combined directly with the sample being loaded onto the gel. The sample may also be combined with a density agent, such as glycerol, which aids in keeping the sample from diffusing out of the well prior to application of the electrical current. Buffer may also be used to stabilize the pH of the sample being run (e.g., Tris, e.g., Tris pH 8.8).

Before a SDS-PAGE is run, proteins may be boiled in the presence or absence of a reducing agent, such as dithiothreitol (DTT) or 2-mercaptoethanol (beta-Mercaptoethanol/BME), which denatures the proteins and dissolves SDS in the sample. The presence of a reducing agent will, for example, reduce and break disulfide bonds between cysteine residue sidechains.

Methods for making and running such gels are well within the knowledge and skill in the art.

Antibodies

The present invention comprises methods for expressing antibodies in cells incubated in growth media which has been evaluated for the present of protease activity. If no significant or detectable protease activity is present, then the growth media is used to propagate the cells.

The term "anti-IGF1R antibody" or "anti-IL-10 antibody" includes any such antibody. In an embodiment of the invention, the anti-IGF1R antibody is any set forth in published U.S. patent application no. US2004/0018191.

Any suitable method can be used to elicit an anti-IGF1R antibody. Description of techniques for preparing monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y.

Mammalian cell lines available as hosts for expression of antibodies of the invention are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, plant cells and fungal cells. Expression of immunoglobulins in bacterial cells, e.g., *E. coli*, is also of interest (see Cabilly, U.S. Pat. No. 4,816,567; and Queen et al. (1989) Proc. Nat'l Acad. Sci. USA 86:10029-10033).

Immunoglobulin/antibody chains can be expressed in a suitable cell by introduction of an expression plasmid into the cell, followed by culturing the cell in a suitable culture medium which has been previously determined, using a method of the present invention, to not contain significant levels of protease (e.g., no detectable levels of protease). When recombinant expression vectors encoding immunoglobulins are introduced into host cells, the antibodies are, in an embodiment of the invention, produced by culturing the host cells for a period of time sufficient to allow for expression of the antibody in the host cells or secretion of the antibody into the culture medium in which the host cells are grown.

Antibodies can be recovered from the culture medium using standard protein purification methods (e.g., chromatography (e.g., reverse phase chromatography, cation exchange, anion exchange, hydroxyapatite, protein A)). Further, expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. The use of matrix attachment regions (MARs) in expression plasmids has also been shown to increase expression levels.

A convenient plasmid system useful for producing an anti-IGF1R antibody or antigen-binding fragment thereof (e.g., Fab, F(ab)$_2$, Fv, ScFv, dsFv) is set forth in published U.S. application no. US2005/0176099 (see also WO2005/47512).

In an embodiment of the invention, an anti-IGF1R antibody or antigen-binding fragment thereof comprises a mature 19D12/15H12 Light Chain-C, D, E or F (LCC, LCD, LCE or LCF) and/or a mature 19D12/15H12 heavy chain-A or B (HCA or HCB). In an embodiment of the invention, the antibody or fragment comprises the mature LCF and the mature HCA (LCF/HCA). In an embodiment of the invention, an IGF1R inhibitor that is administered to a patient in a method according to the invention is an isolated antibody that specifically binds to IGF1R that comprises one or more complementarity determining regions (CDRs) of 19D12/15H12 Light Chain-C, D, E or F and/or 19D12/15H12 heavy chain-A or B (e.g., all 3 light chain CDRs and all 3 heavy chain CDRs).

The amino acid and nucleotide sequences of the some antibody chains of the invention are shown below. Dotted, underscored type indicates the signal peptide. Solid underscored type indicates the CDRs. Plain type indicates the framework regions. Mature fragments lack the signal peptide.

```
Modified 19D12/15H12 Light Chain-C (SEQ ID NO: 1):
ATG TCG CCA TCA CAA CTC ATT GGG TTT CTG CTG CTC TGG GTT CCA GCC TCC
AGG GGT GAA ATT GTG CTG ACT CAG AGC CCA GAC TCT CTG TCT GTG ACT CCA
GGC GAG AGA GTC ACC ATC ACC TGC CGG GCC AGT CAG AGC ATT GGT AGT AGC
TTA CAC TGG TAC CAG CAG AAA CCA GGT CAG TCT CCA AAG CTT CTC ATC AAG
TAT GCA TCC CAG TCC CTC TCA GGG GTC CCC TCG AGG TTC AGT GGC AGT GGA
TCT GGG ACA GAT TTC ACC CTC ACC ATC AGT AGC CTC GAG GTC GAA GAT GCT
GCA GCG TAT TAC TGT CAT CAG AGT AGT CGT TTA CCT CAC ACT TTC GGC CAA
GGG ACC AAG GTG GAG ATC AAA CGT ACG SEQ ID NO: 2:
M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D A
A A Y Y C H Q S S R L P H T F G Q
G T K V E I K R T Modified 19D12/15H12 Light Chain-D (SEQ ID NO: 3):
ATG TCG CCA TCA CAA CTC ATT GGG TTT CTG CTG CTC TGG GTT CCA GCC TCC
AGG GGT GAA ATT GTG CTG ACT CAG AGC CCA GAC TCT CTG TCT GTG ACT CCA
GGC GAG AGA GTC ACC ATC ACC TGC CGG GCC AGT CAG AGC ATT GGT AGT AGC
TTA CAC TGG TAC CAG CAG AAA CCA GGT CAG TCT CCA AAG CTT CTC ATC AAG
TAT GCA TCC CAG TCC CTC TCA GGG GTC CCC TCG AGG TTC AGT GGC AGT GGA
TCT GGG ACA GAT TTC ACC CTC ACC ATC AGT AGC CTC GAG GCT GAA GAT TTC
GCA GCG TAT TAC TGT CAT CAG AGT AGT CGT TTA CCT CAC ACT TTC GGC CAA
GGG  ACC AAG GTG GAG ATC AAA CGT ACG SEQ ID NO: 4:
M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D F
A V Y Y C H Q S S R L P H T F G Q
G T K V E I K R T Modified 19D12/15H12 Light Chain-E (SEQ ID NO: 5):
ATG TCG CCA TCA CAA CTC ATT GGG TTT CTG CTG CTC TGG GTT CCA GCC TCC
AGG GGT GAA ATT GTG CTG ACT CAG AGC CCA GAC ACC CTG TCT GTG TCT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GAA GAT GCT
GCA GCG TAT TAC TGT CAT CAG AGT AGT CGT TTA CCT CAC ACT TTC GGC CAA
GGG ACC AAG GTG GAG ATC AAA CGT ACA SEQ ID NO: 6:
M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D A
A A Y Y C H Q S S R L P H T F G Q
G T K V E I K R T Modified 19D12/15H12 Light Chain-F (SEQ ID NO: 7):
ATG TCG CCA TCA CAA CTC ATT GGG TTT CTG CTG CTC TGG GTT CCA GCC TCC
AGG GGT GAA ATT GTG CTG ACT CAG AGC CCA GGT ACC CTG TCT GTG TCT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GAA GAT TTC
GCA GTG TAT TAC TGT CAT CAG AGT AGT CGT TTA CCT CAC ACT TTC GGC CAA
GGG ACC AAG GTG GAG ATC AAA CGT ACA
```

-continued

SEQ ID NO: 8:
M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D F
A V Y Y C H Q S S R L P H T F G Q
G T K V E I K R T

Modified 19D12/15H12 heavy chain-A (SEQ ID NO: 9):
ATG GAG TTT GGG CTG AGC TGG GTT TTC CTT GTT GCT ATA TTA AAA GGT GTC
CAG TGT GAG GTT CAG CTG GTG CAG TCT GGG GGA GGC TTG GTA AAG CCT GGG
GGC TCC CTG AGA CTC TCC TGT GCA GCC TCT GGA TTC ACC TTC AGT AGC TTT
GCT AGT CAC TGG GTT CGC CAG GCT CCA GGA AAA GGT CTG GAG TGG ATA TCA
GTT ATT GAT ACT CGT GGT GCC ACA TAC TAT GCA GAC TCC GTG AAG GGC CGA
TTC ACC ATC TCC AGA GAC AAT GCC AAG AAC TCC TTG TAT CTT CAA ATG AAC
AGC CTG AGA GCC GAG GAC ACT GCT GTG TAT TAC TGT GCA AGA CTG GGG AAC
TTC TAC TAC GGT ATG GAC GTC TGG GGC CAA GGG ACC ACG GTC ACC GTC TCC
TCA SEQ ID NO: 10:
Met Glu Phe Gly Leu Ser Trp Val Phe Leu Val Ala Ile Leu Lys Gly Val
Gln Cys Glu Val Gln Leu Val Gln Ser Gly Gly Gly Leu Val Lys Pro Gly
Gly Ser Leu Arg Leu Ser Cys Ala Ala Ser Gly Phe Thr Phe Ser Ser Phe
Ala Met His Trp Val Arg Gln Ala Pro Gly Lys Gly Leu Glu Trp Ile Ser
Val Ile Asp Thr Arg Gly Ala Thr Tyr Tyr Ala Asp Ser Val Lys Gly Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg Leu Gly Asn
Phe Tyr Tyr Gly Met Asp Val Trp Gly Gln Gly Thr Thr Val Thr Val Ser
Ser Modified 19D12/15H12 heavy chain-B (SEQ ID NO: 11):
ATG GAG TTT GGG CTG AGC TGG GTT TTC CTT GTT GCT ATA TTA AAA GGT GTC
CAG TGT GAG GTT CAG CTG GTG CAG TCT GGG GGA GGC TTG GTA CAG CCT GGG
GGC TCC CTG AGA CTC TCC TGT GCA GCC TCT GGA TTC ACC TTC AGT AGC TTT
GCT AGT CAC TGG GTT CGC CAG GCT CCA GGA AAA GGT CTG GAG TGG ATA TCA
GTT ATT GAT ACT CGT GGT GCC ACA TAC TAT GCA GAC TCC GTG AAG GGC CGA
TTC ACC ATC TCC AGA GAC AAT GCC AAG AAC TCC TTG TAT CTT CAA ATG AAC
AGC CTG AGA GCC GAG GAC ACT GCT GTG TAT TAC TGT GCA AGA CTG GGG AAC
TTC TAC TAC GGT ATG GAC GTC TGG GGC CAA GGG ACC ACG GTC ACC GTC TCC
TCA SEQ ID NO: 12:
Met Glu Phe Gly Leu Ser Trp Val Phe Leu Val Ala Ile Leu Lys Gly Val
Gln Cys Glu Val Gln Leu Val Gln Ser Gly Gly Gly Leu Val Gln Pro Gly
Gly Ser Leu Arg Leu Ser Cys Ala Ala Ser Gly Phe Thr Phe Ser Ser Phe
Ala Met His Trp Val Arg Gln Ala Pro Gly Lys Gly Leu Glu Trp Ile Ser
Val Ile Asp Thr Arg Gly Ala Thr Tyr Tyr Ala Asp Ser Val Lys Gly Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg Leu Gly Asn
Phe Tyr Tyr Gly Met Asp Val Trp Gly Gln Gly Thr Thr Val Thr Val Ser
Ser

EXAMPLES

The following example is provided to further describe the present invention and should not be construed as a limitation thereof. The scope of the present invention includes any and all compositions and methods described in the example.

Example 1

Proteolysis Assay

In this example, the proteolytic activity of a sample of growth media was assayed using an anti-IL-10 or an anti-IGF1R monoclonal antibody as a polypeptide substrate. The growth media used was a chemically defined media into which a hydrolysate was added. The hydrolysate was the source of the proteolytic activity that was determined.

This example demonstrates that while conventional proteolysis analysis techniques are not sufficient for detecting the low levels of proteolytic activity present in the hydrolysate used, the assays of the present invention are sufficiently sensitive and, thus, well suited for this purpose.

SDS-PAGE gel. Gels containing 4-12% polyacryamide (stacking gel-resolving gel) were used for non-reducing SDS-PAGE, and gels containing 4-20% polyacryamide (stacking gel-resolving gel) were used for reducing SDS-PAGE.

1.5M Tris pH 8.8: Dissolved 90.73 g Tris base in 400 ml DI $H_2O$. Adjusted pH to 8.8 with hydrochloric acid. Brought solution to a volume of 500 ml with DI $H_2O$. Stored at 4° C.

pH 8.8 Sample Buffer. Combined the following: 228 ml of DI $H_2O$, 50 ml glycerol, 50 ml 1.5M Tris pH 8.8, 50 ml 10% SDS solution, and 10 ml 0.05% bromophenol blue. Stored at 4° C.

2× reducing sample buffer. Prepared 3% by volume 2-Mercaptoethanol in pH 8.8 sample Buffer. Prepared fresh prior to use.

Non-reducing sample buffer. Novex Tris-Glycine SDS Sample Buffer 2× (Invitrogen; Carlsbad, Calif.): 126 mM Tris HCl pH 6.8, 20% glycerol, 4% SDS, 0.005% bromophenol blue was purchased commercially.

Sample preparation and analysis. Chemically defined media (CD3) was spiked with soy or wheat hydrolysate sample at a final concentration of 15 g/L. The antibody substrate (in 5 mM sodium acetate pH 5.5) was then spiked into this mixture at a final concentration of 1 mg/ml.

For the reducing and non-reducing assays, the reducing or non-reducing buffers were combined with the media/antibody mixtures (above) in equal volumes and incubated overnight (18 hours) at room temperature (23° C.). After incubation for 5 hours or overnight (about 18 hours), the mixture was boiled at 90° C. for 5 minutes. The boiled mixture was then analyzed by SDS-PAGE. Approximately 10 ug of protein were loaded into each well of the gel. The mixtures were quickly boiled again immediately before loading onto the gel. Electrophoresis was performed with the XCell Surelock™ Mini-Cell system (Invitrogen; Carlsbad, Calif.) at a constant voltage of 125 mV for 90 minutes.

CD3 is chemically-defined cellular growth media which is commercially available from Sigma-Aldrich (St. Louis, Mo.). CD3 contains inorganic salts, HEPES and sodium bicarbonate buffers, essential and non-essential amino acids, vitamins, recombinant human insulin, other organic compounds, trace elements, and surfactants. CD3 does not contain antibiotics, antimycotics, L-glutamine, transferrin, hydrolysates, or other undefined nutrients or supplements. CD3 also contains no animal-derived components or components synthesized from animal-derived materials.

Experiments.

Four experiments were performed as follows.

(1) Comparison of assay sensitivity with incubation of reaction mixture for 5 hours or overnight (18 hours)-reducing gel. The substrate used was anti-IGF1R antibody. Four pairwise trials were performed, wherein incubation was for 5 hours or overnight, and the reducing SDS-PAGE gel that resulted is set forth in FIG. 1. The arrows in FIG. 1 indicate the presence of proteolytic products. Under reducing gel conditions, the products were visible in two of the trials wherein incubation was performed overnight but not visible in the same trial wherein incubation was for only 5 hours. These data established that incubation of the mixture overnight increased the ability to observe low level proteolytic products, and thus assay sensitivity, beyond that observed when the incubation occurred for only 5 hours.

Figure 2:
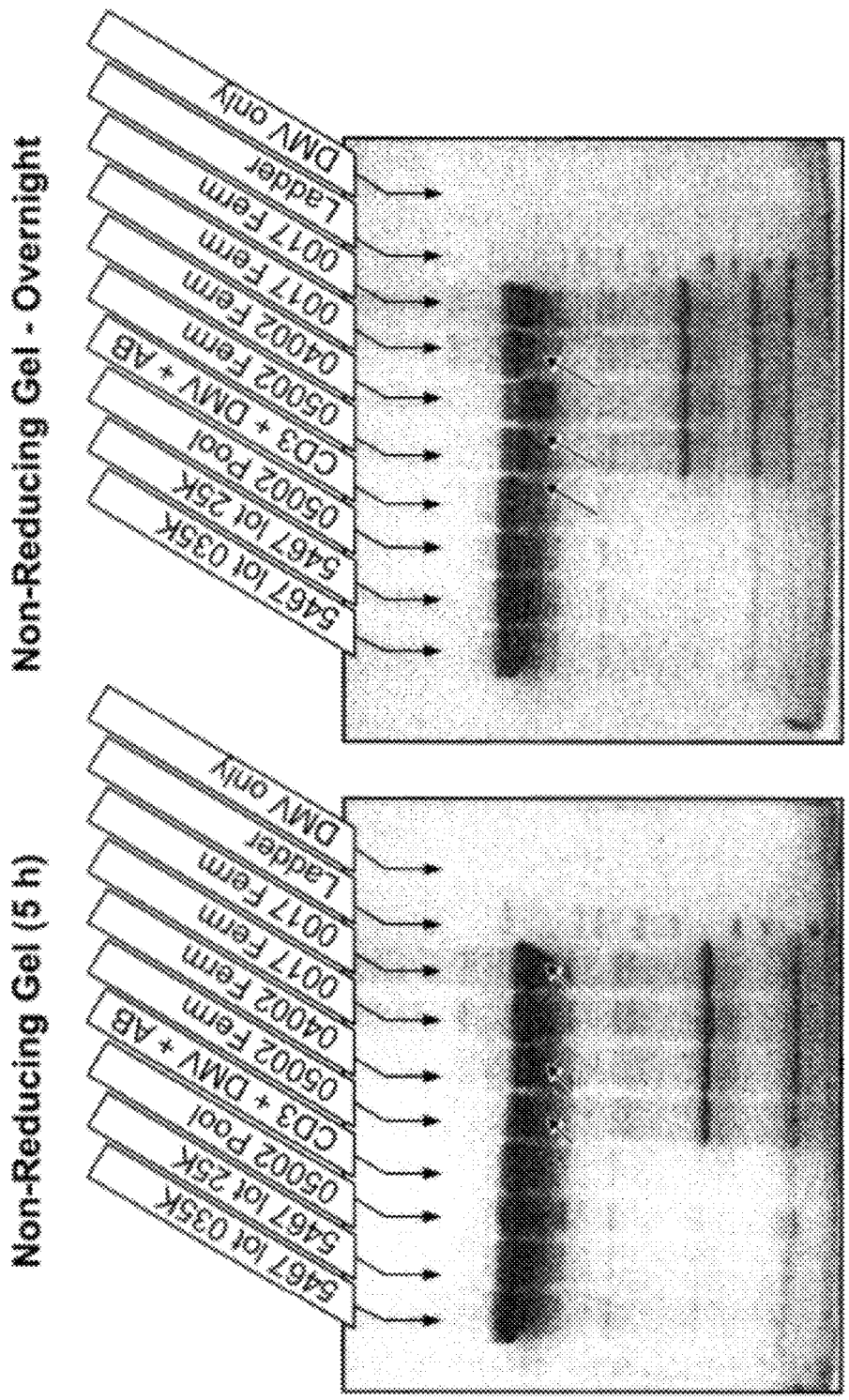
FIG. 2: Example of increased sensitivity with exposure time for non-reducing gels. Arrows indicate lanes of increased proteolysis with exposure time.

(2) Comparison of assay sensitivity with incubation for 5 hours or overnight-non-reducing gel. Again, the substrate was anti-IGF1R antibody. Eight trials were performed with incubation for 5 hours or overnight. The non-reducing SDS-PAGE gel results are set forth in FIG. 2. The arrows in FIG. 2 indicate the presence of proteolytic products. Under the non-reducing conditions greater levels of proteolysis were evidence after overnight incubation than were evidence after only 5 hours of incubation. These data also confirmed that overnight incubation of the mixture led to an increased level of assay sensitivity.

Figure 3:
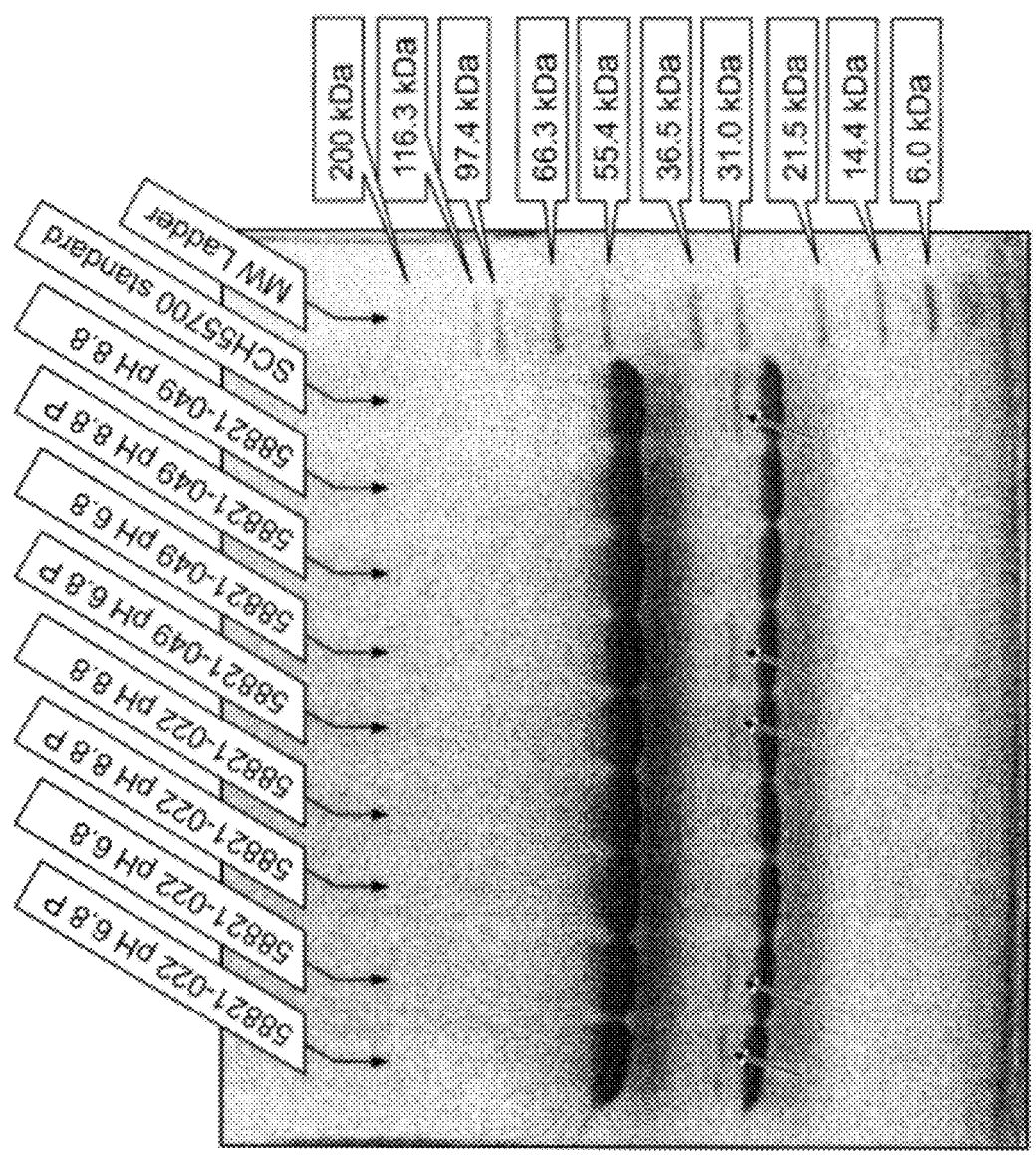
FIG. 3: Example of the effects of buffer pH for determining proteolytic activity. These samples were for anti-IL10. No protease activity was present in these samples, but the pH 6.8 buffer produced fragments that appeared as proteolysis, thereby producing false positives (arrows) as described in the text.

(3) Comparison of gel sensitivity and quality after incubation at pH 6.8 or 8.8. The material analyzed in this experiment was anti-IL-10 antibody which has been purified and is free of proteases. Four pairwise trials were conducted wherein the pH was 6.8 (Laemmli method) or 8.8 under protease-free conditions. The results of the comparison are set forth in the SDS-PAGE gel of FIG. 3. When the incubation was performed at pH 8.8, false positive protein bands in the SDS-PAGE gel were not visible. The false positive bands were, however, visible at pH 6.8.

Figure 4:
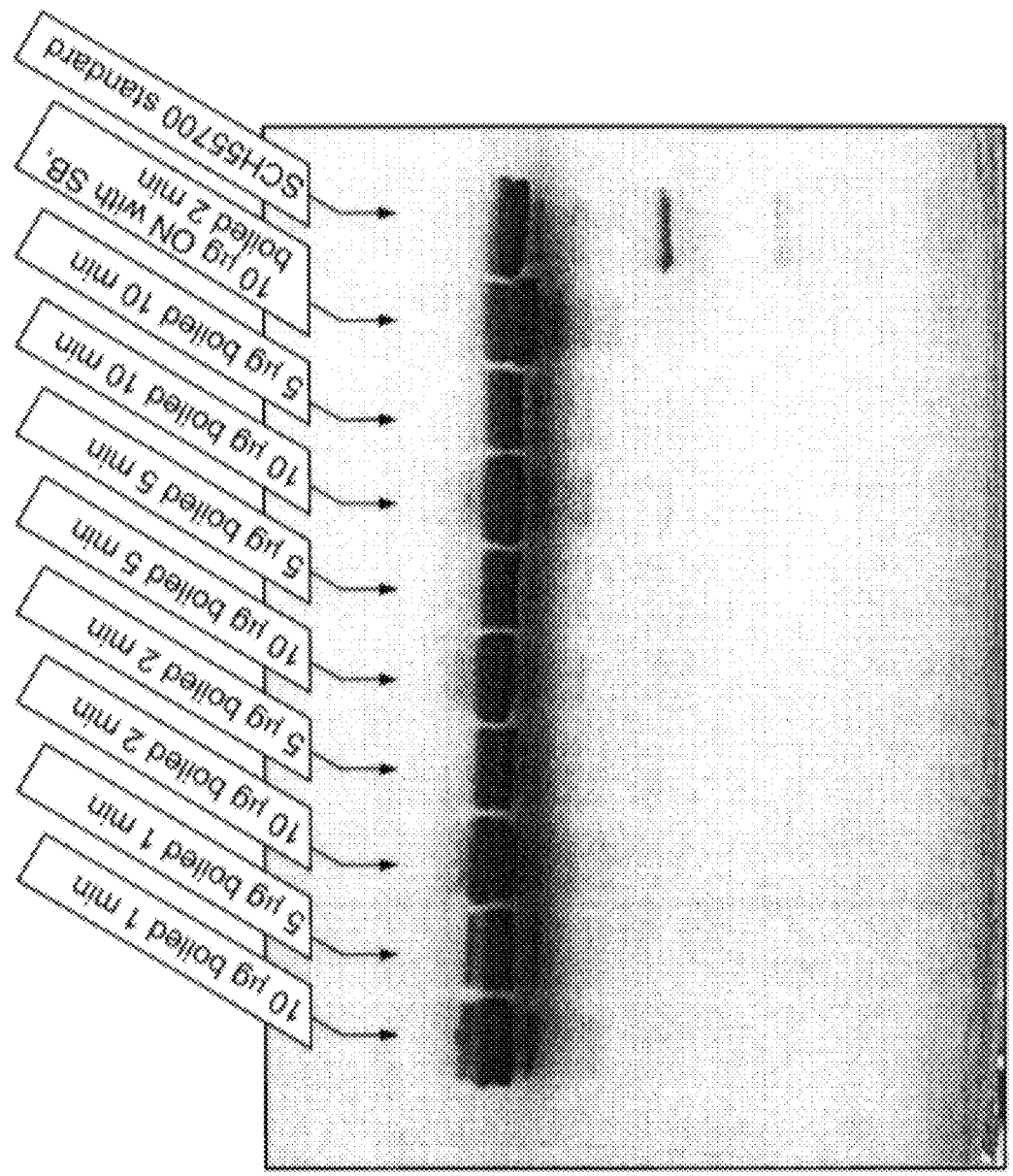
FIG. 4: The boiling time was optimized. Proteolytic enzymes are denatured after 5 minutes at 90° C. These samples were boiled immediately after sample preparation with the exception of Lane 9.

(4) Determination of boiling time required to inactivate proteases in reaction mixture. The substrate was anti-IL-10 antibody. Four pairwise trials were performed wherein either 5 or 10 μg of antibody substrate was present. Samples were boiled for 1, 2, 5 or 10 minutes immediately after preparation. An additional trial was also performed wherein the sample was not boiled until after overnight incubation. The results of the SDS-PAGE analysis are set forth in FIG. 4. The proteolytic activity in the sample was inactivated after 5 minutes of boiling. These data indicate that boiling the sample before an overnight incubation would render the sample free of protease activity and, thus, would not lead to accurate results with respect to measuring the protease activity in a sample. For this reason, omitting any boiling step prior to the overnight incubation of the sample and substrate is desirable.

Example 2

Analysis of Degradation of Anti-IGF1R by Growth Medium

In this example, the present protease assay was used to evaluate several culture components for proteolytic activity against anti-IGF1R antibody. Using inhibition experiments, it also demonstrates that the fragments detected are indeed from enzymes present in solution instead of being artifacts from the assay itself, as previously seen at pH 6.8.

Animal-component free C5467 CHO medium, animal-component free imMEDIAte Advantage™ CHO medium (without aurintricarboxylic acid (ATA) or hydrolysates) and 1615 CHO medium supplement (Sterile filtered feed concentration containing amino acids, vitamins, recombinant human insulin, plant hydrolysates, trace elements and other organic compounds; lacking glucose, L-glutamine, phenol red, antibiotics, antimycotics, or transferrin hypoxanthine and thymidine) were obtained from Sigma-Aldrich (St. Louis, Mo.). Hypep 4601S wheat hydrolysates were obtained from Kerry Biosciences (AH Almere, The Netherlands). Ethylenediaminetetraacetic acid (EDTA), trans-epoxy-succinyl-L-leucylamido-(4-guanidino)butane (E-64), was obtained from EMD Biosciences.

Gels containing 4-20% polyacryamide were used for reducing SDS-PAGE. Recipes for buffers were as follows:

1.5M Tris pH 8.8: Dissolve 90.73 g Tris base in 400 ml DI $H_2O$. pH to 8.8 with Hydrochloric Acid. Bring to volume of 500 ml with DI $H_2O$, Store at 4° C. (This is one of the components used to make pH 8.8 Sample Buffer—below)

pH 8.8 Sample Buffer: Combine the following: 228 ml of DI $H_2O$, 50 ml Glycerol, 50 ml 1.5M Tris pH 8.8, 50 ml 10% SDS solution, and 10 ml 0.05% Bromophenol Blue. Store at 4° C.

2× Reducing Sample Buffer: Prepare 3% by volume 2-Mercaptoethanol in pH 8.8 Sample Buffer. Prepare fresh prior to use.

The buffers were combined with the samples in equal volumes and allowed to sit overnight at room temperature before boiling. This increases the sensitivity of the assay for protease activity. The samples were then boiled directly before submitting for SDS-PAGE.

E-64 was dissolved in DMSO and EDTA was dissolved in sterile distilled water. Samples were allowed to incubate overnight at room temperature. Samples were then combined in equal parts with anti-IGF1R drug substance to yield a final concentration of 0.5 mg/ml antibody. Reducing buffer was added in equal parts to the samples containing antibody. Following overnight incubation, these samples were then loaded onto gels for reducing SDS-PAGE for a final load of 10-12 μg of antibody. Inhibition studies were also performed with samples not containing antibody on the zymograms in order to determine the molecular weight of the inhibited protease. Concentrations of some thiol-proteases were predicted by inhibiting a papain control with E-64. All inhibitors were allowed to remain at room temperature with the samples overnight before loading onto the gels.

Figure 5:
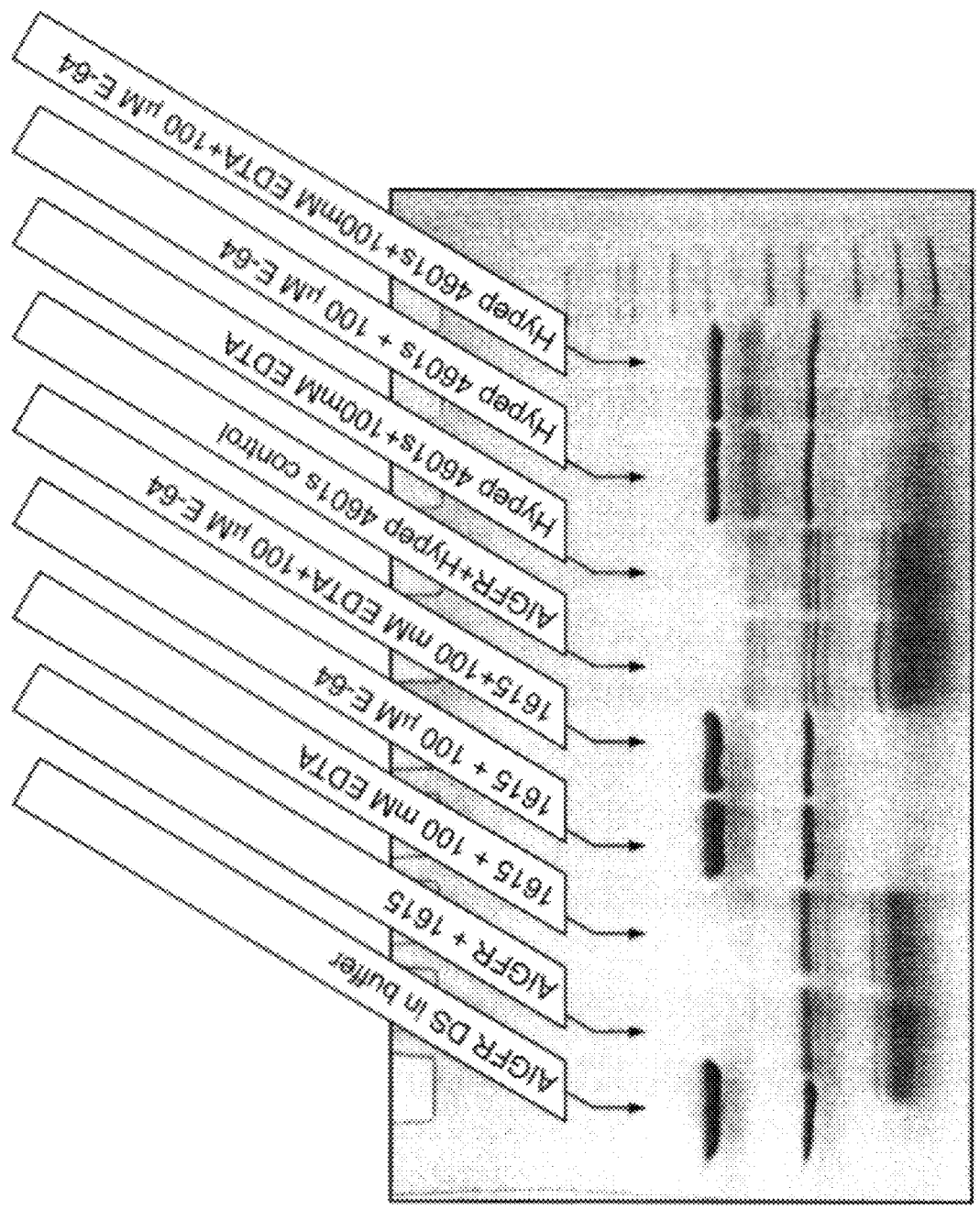
FIG. 5: Inhibition experiments with 1615 media supplement and Kerry Hypep 4601S hydrolysates via reducing SDS-PAGE. Lane 1: Anti-IGF1R without protease; Lane 2: Anti-IGF1R+1615 (1615) culture supplement; Lane 3: Anti-IGF1R+1615+EDTA; Lane 4: Anti-IGF1R+1615+E-64 protease inhibitor; Lane 5: Anti-IGF1R+1615+EDTA+E-64 protease inhibitor; Lane 6: Anti-IGF1R+Hypep 4601s protein hydrolysate; Lane 7: Anti-IGF1R+Hypep 4601s protein hydrolysate+EDTA; Lane 8: Anti-IGF1R+Hypep 4601s protein hydrolysate+E-64 protease inhibitor; Lane 9: Anti-IGF1R+Hypep 4601s protein hydrolysate+EDTA+E-64 protease inhibitor; Lane 10: molecular weight markers.

Inhibition experiments with 1615 revealed an active thiol-protease that was inhibited by 100 μM E-64 (FIG. 5).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method for reducing the appearance of false positive bands in SDS-PAGE analysis of proteolytic digestion of a sample that comprises an immunoglobulin polypeptide; comprising incubating a mixture comprising the sample and the immunoglobulin polypeptide, for at least about 8 hours at a pH that causes fewer false positive bands in said SDS-PAGE analysis relative to pH 6.8, wherein said pH is 8.8, subjecting the mixture to electrophoresis on an SDS-PAGE gel and staining the gel with a protein indicator dye.

2. The method of claim 1 wherein the incubated mixture comprises a reducing agent.

3. The method of claim 1 wherein the gel is a 4-12% or 4-20% discontinuous SDS-polyacrylamide gel.

4. The method of claim 1 wherein about 12 μg of the peptide substrate is electrophoresed on the gel.

5. The method of claim 1 wherein the incubated mixture comprises Tris pH 8.8 buffer.

6. The method of claim 1 wherein the incubated mixture is incubated for about 18 hours.

7. The method of claim 1 wherein the concentration of the immunoglobulin polypeptide in the incubated mixture is about 1 mg/ml.

8. The method of claim 1 wherein the incubation is carried out at room temperature.

9. The method of claim 1 wherein the immunoglobulin polypeptide is from an anti-IGF1R antibody or an anti-IL10 antibody.

10. The method of claim 1 wherein the sample is cellular growth media.

11. The method of claim 10 wherein the growth media comprises a hydrolysate.

12. The method of claim 11 wherein the hydrolysate is a plant-derived hydrolysate.

* * * * *